(12) United States Patent
Horie et al.

(10) Patent No.: US 7,094,797 B2
(45) Date of Patent: Aug. 22, 2006

(54) ORGAN FIBROSIS INHIBITOR

(75) Inventors: Takashi Horie, Kawasaki (JP);
Megumi Nakajoh, Kawasaki (JP);
Ichiro Sonaka, Kawasaki (JP); Sonoko Ishizaki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/875,274

(22) Filed: Jun. 25, 2004

(65) Prior Publication Data

US 2005/0020656 A1 Jan. 27, 2005

Related U.S. Application Data

(63) Continuation of application No. PCT/JP02/13420, filed on Dec. 24, 2002.

(30) Foreign Application Priority Data

Dec. 25, 2001 (JP) .............................. 2001-392464
Mar. 20, 2002 (JP) .............................. 2002-077603

(51) Int. Cl.
*A61K 31/415* (2006.01)
*A61K 31/195* (2006.01)

(52) U.S. Cl. ...................................... 514/400; 514/562

(58) Field of Classification Search ..................... None
See application file for complete search history.

(56) References Cited

U.S. PATENT DOCUMENTS

| | | | | |
|---|---|---|---|---|
| 2,829,056 A | * | 4/1958 | Kemmerer | .................. 426/649 |
| 4,279,917 A | * | 7/1981 | Takami et al. | .............. 514/400 |
| 4,499,076 A | | 2/1985 | Ohashi et al. | |
| 5,032,608 A | * | 7/1991 | Dudrick | ....................... 514/396 |
| 5,352,691 A | | 10/1994 | Thomas | |
| 5,571,783 A | * | 11/1996 | Montagne et al. | .............. 514/2 |
| 5,658,937 A | * | 8/1997 | Thomas | ...................... 514/400 |
| 5,670,201 A | * | 9/1997 | Takahashi et al. | ........... 426/648 |
| 5,719,133 A | | 2/1998 | Schmidl et al. | |
| 5,741,807 A | * | 4/1998 | Thomas | ...................... 514/399 |
| 5,922,766 A | | 7/1999 | Acosta et al. | |
| 5,955,450 A | * | 9/1999 | Breborowicz et al. | ......... 514/54 |
| 6,329,414 B1 | | 12/2001 | Thomas et al. | |
| 2003/0087870 A1 | * | 5/2003 | Gilbertson | ..................... 514/44 |

OTHER PUBLICATIONS

The Merck Index, 11th edition, published 1989, pp. 436, "cysteine" and "cystine", 685 "Gelatin" and 746 "Histidine".*
Stedman's Medical Dictionary, 25th Ed. published 1990, pp 1097-1098, "organ".*
The Merck Manual of Diagnosis and Therapy, 14th edition, published 1982, pp 386-389 and 634-639.*
Wang, et al., *Biosci. Biotechnol. Biochem.*, vol. 63, No. 2, pp. 319-322 (1999).

* cited by examiner

*Primary Examiner*—Raymond J. Henley, III
(74) *Attorney, Agent, or Firm*—Oblon, Spivak, McClelland, Maier & Neustadt, P.C.

(57) ABSTRACT

An organ fibrosis inhibitor, in particular, a liver fibrosis inhibitor is provided, which contains histidine, preferable together with cysteine and/or cystine as active ingredients. Owing to the combined use, a remarkable effect of inhibiting organ fibrosis, in particular, liver fibrosis can be shown. These substances are usable as the desired active ingredients in the form of a drug or in the form of a food and drink. There is also provided an organ fibrosis inhibitor comprising the active ingredients as described above either separately or as a combination of one of them with a mixture of the other two ingredients. Thus, it is possible to present organ fibrosis inhibitors such as a liver fibrosis inhibitor which are applicable in the form used in health foods for improving and maintaining liver function and foods and drinks for sick people, as well as drugs for various organ diseases caused by fibrosis such as liver diseases.

21 Claims, 5 Drawing Sheets mean ± standard deviation mean + standard deviation

ORGAN FIBROSIS INHIBITOR

CROSS REFERENCES TO RELATED APPLICATIONS

This application is a continuation of PCT International Patent Application No. PCT/JP02/13420, filed on Dec. 24, 2002, and claims priority to Japanese Patent Application Nos. 2001-392464, filed on Dec. 25, 2001, and 2002-077603, filed on Mar. 20, 2002, all of which are incorporated herein by reference in their entireties.

BACKGROUND OF THE INVENTION

1. Field of the Invention

The present invention relates to novel organ fibrosis inhibitors, including kidney fibrosis inhibitors, pancreas fibrosis inhibitors, lung fibrosis inhibitors, vascular vessel fibrosis inhibitors, skin fibrosis inhibitors, bone marrow fibrosis inhibitors, liver fibrosis inhibitors, and the like. The invention also relates to organ fibrosis inhibitors which can be orally given or orally ingested and to pharmaceutical agents for various organ diseases due to fibrosis, particularly pharmaceutical agents (medical products) for liver diseases such as liver fibrosis and cirrhosis and to food and drink products such as food products for health use and food products for sick individuals.

Additionally, the present invention relates to methods for suppressing organ fibrosis, including methods for the therapeutic treatment, amelioration, progress prevention and prophylaxis of diseases due to organ fibrosis in biological organisms. The present invention further relates to methods of producing such organ fibrosis inhibitors, including forms such as medical products and food and drink products, and a combination of the plural active ingredients as an organ fibrosis inhibitor or a combination thereof for use in the method for suppressing organ fibrosis in the case when these active ingredients are used, and the like.

2. Discussion of the Background

To date, no pharmaceutical agents (prophylactic, ameliorating and/or therapeutic agent) effective as an organ fibrosis inhibitor, particularly a pharmaceutical agent for liver diseases such as liver fibrosis and cirrhosis have been reported.

For example, cirrhosis is not only the terminal stage of chronic liver diseases such as viral or alcoholic hepatitis, but also progresses highly frequently to hepatocellular carcinoma. Therefore, the development of a direct therapeutic method for liver fibrosis as a cause of cirrhosis is desired, in addition to existing therapeutic methods for the complications (ascites, edema, encephalopathy, jaundice).

Liver fibrosis is thought to be an outcome of excess deposition of extracellular matrices such as collagen during the repair of liver tissue when the balance is lost between hepatocyte necrosis triggered by an external factor, such as a virus and alcohol, or an internal factor involving autoimmune abnormality, and liver regeneration to maintain liver functions. At the cellular level, hepatocyte disorders and necrosis activate Kupffer's cells, endothelial cells and the like, so that TNF-α, TGF-β, and PDGF are released from the activated Kupffer's cells and endothelial cells. It is considered that those factors then activate Hepatic stellate cells as the main factor of liver fibrosis, so that cellular growth and collagen synthesis are triggered.

Even in organs such as the lungs, kidneys, pancreas, and skin, similarly to the liver, it is believed that fibroblasts existing in the individual organs and stromal cells specific to the individual organs (kidney mesangial cells, pancreatic stellate cells, etc.) lapse into abnormal growth and extracellular matrix synthesis due to the stimulation by various cytokines, leading to the occurrence of organ fibrosis.

Therefore, the development of a pharmaceutical agent with a significant direct efficacy on liver fibrosis is needed. Additionally, the development of a pharmaceutical agent effective for the inhibition of fibrosis in various organs in addition to the liver is also needed.

Thus, there remains a need for agents and methods for inhibiting organ fibrosis.

SUMMARY OF THE INVENTION

Accordingly, it is one object of the present invention to provide novel agents which are effective for suppressing organ fibrosis.

It is another object of the present invention to provide novel agents which are particularly effective for suppressing liver fibrosis It is another object of the present invention to provide novel pharmaceutical agents which are useful not only in the form of medical products, such as pharmaceutical agents for various diseases of organs including the liver, but also in forms used in food and drink products such as food products for health use and/or food products for sick people.

It is another object of the present invention to provide novel methods for treating, ameliorating, suppressing, inhibiting, and/or preventing organ fibrosis.

It is another object of the present invention to provide novel methods for treating, ameliorating, suppressing, inhibiting, and/or preventing liver fibrosis.

These and other objects, which will become apparent during the following detailed description, have been achieved by the inventors' discoveries that:

(1) histidine (L-histidine, D-histidine, DL-histidine, and the like) exert an action of suppressing organ fibrosis, particularly the action of suppressing liver fibrosis;

(2) histidine when used as an active ingredient is applicable not only in forms of medical products such as pharmaceutical agents for diseases of various organs such as liver diseases but also in forms used in food or drink products such as food products for health use and food products for sick individuals;

(3) particularly when cysteine (L-cysteine, D-cysteine, DL-cysteine, and the like) and/or cystine (L-cystine, D-cystine, DL-cystine, and the like) is used as an active ingredient in combination with the histidine, the mixture can exert an even stronger action for suppressing fibrosis; and the like.

Based on these individual findings, the invention has been achieved.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

mean+standard deviation for normal (N=4), control (N=7) and His-dosed group (N=8); and

Figure 2:
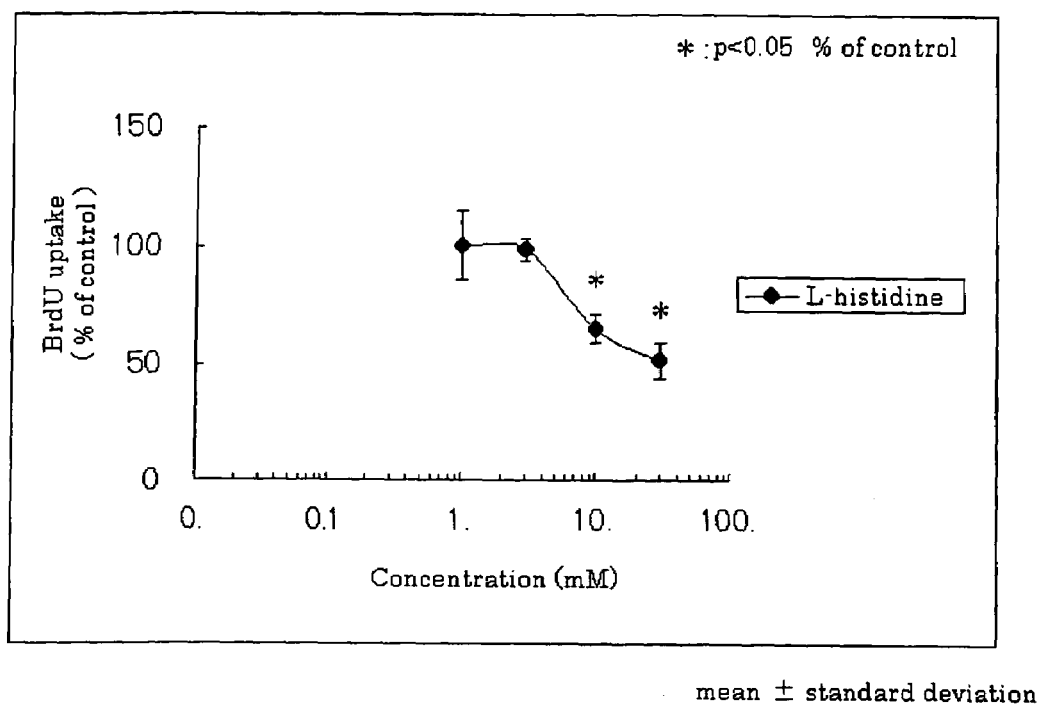
Figure 3:
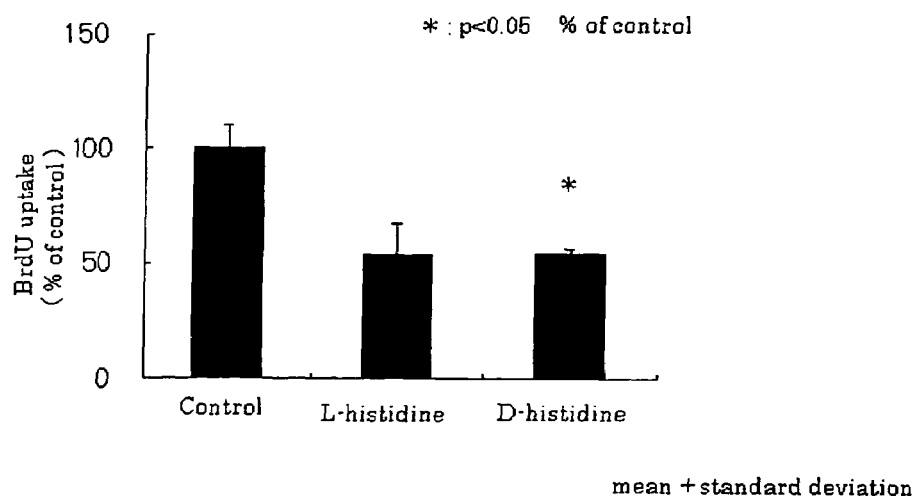
Figure 4:
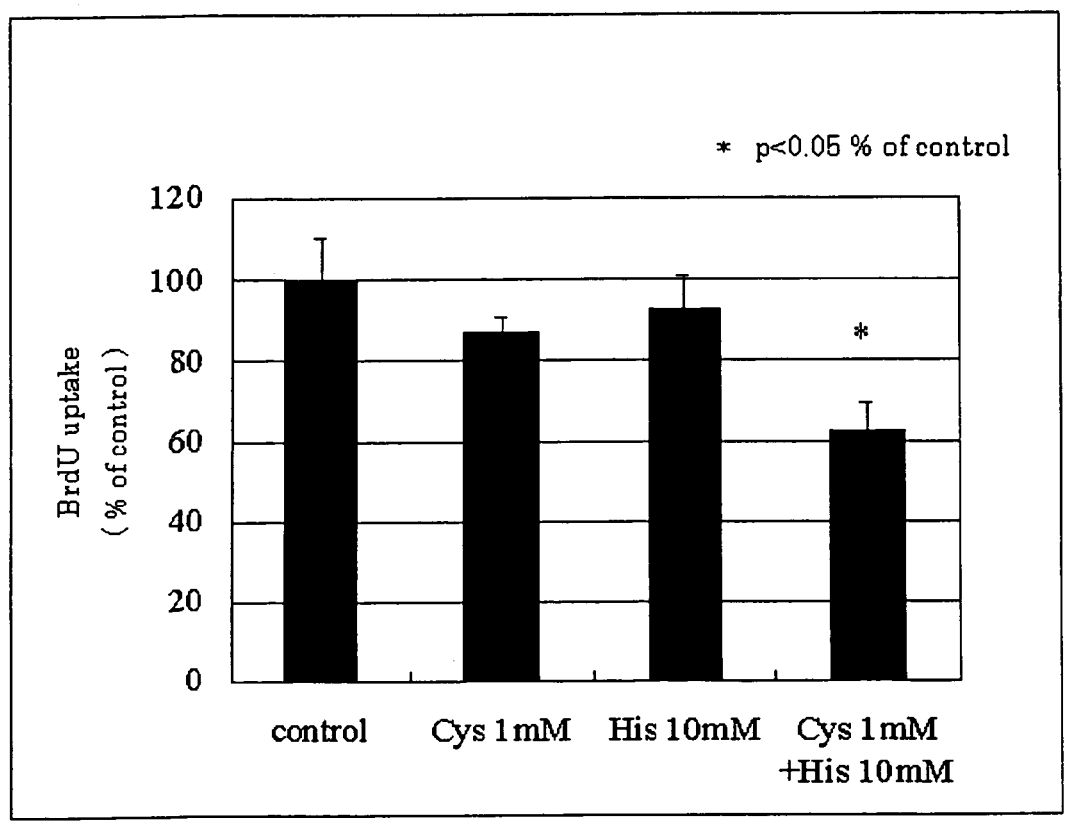
Figure 5A:
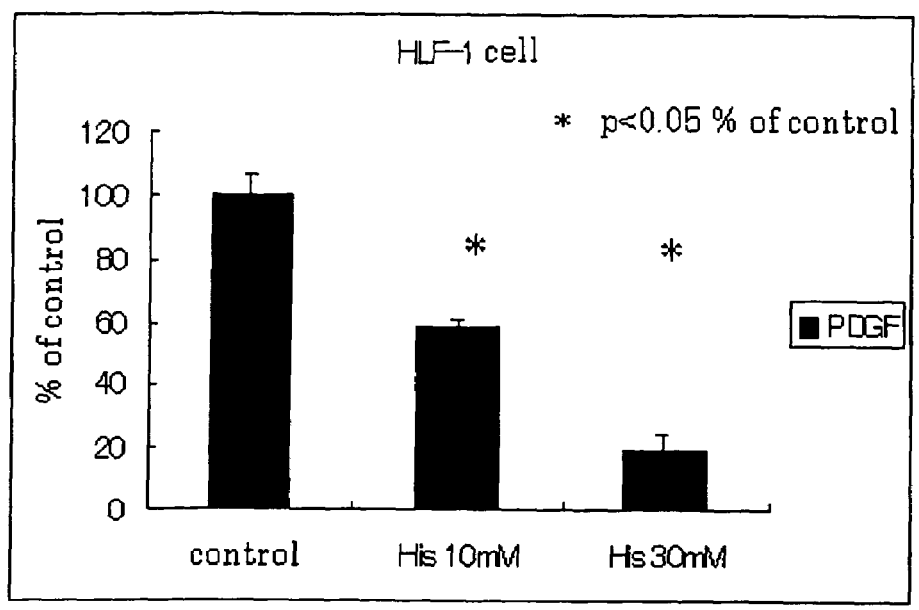
Figure 5B:
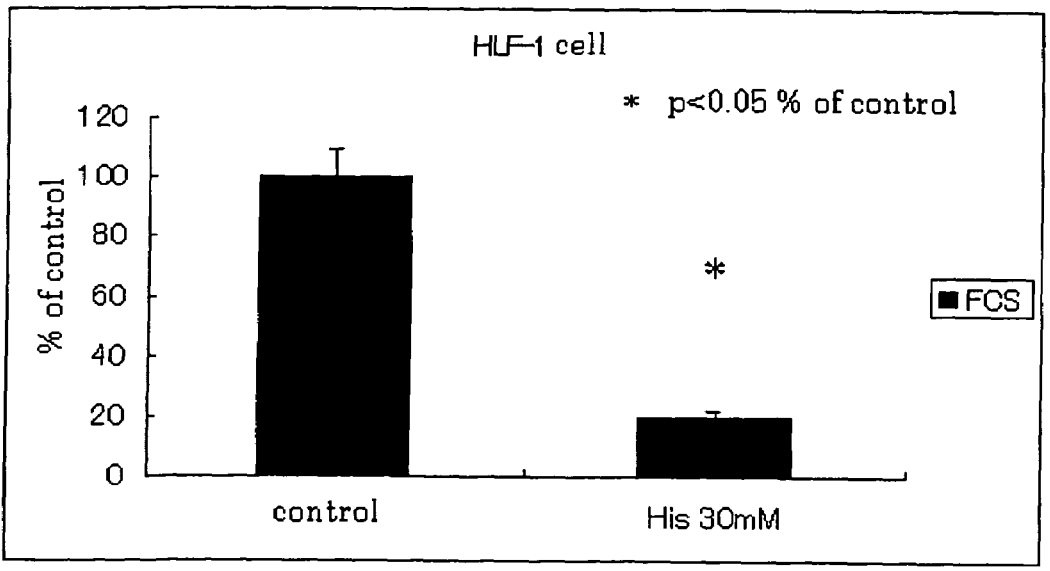

*: $p<0.05$ by Dunnet's multiple test;

FIG. 2 depicts the results of the assay of DNA synthesis ability of Hepatic stellate cells due to the stimulation with the platelet-derived growth factor reported in Example 2, where mean±standard deviation (N=3);

*: $p<0.05$ by the t-test;

FIG. 3 depicts the results of the assay of DNA synthesis ability of Hepatic stellate cells due to the stimulation with the platelet-derived growth factor reported in Example 3, where mean+standard deviation (N=3);

*: $p<0.05$ by the t-test;

FIG. 4 depicts the results of the assay of DNA synthesis ability of Hepatic stellate cells due to the stimulation with the platelet-derived growth factor reported in Example 4 (the combined effect of Cys and His on the PDGF-stimulated DNA synthesis ability of rat Hepatic stellate cells), where mean+standard deviation (N=3);

*: $p<0.05$ by the t-test;

FIGS. 5a and 5b depict the results of the assay of BrdU uptake into cells reported in Example 5, where FIG. 5a depicts the case with PDGF addition; and FIG. 5b depicts the case with FCS addition;

mean+standard deviation (N=3);

*: $p<0.05$ by the t-test; and

Figure 6:
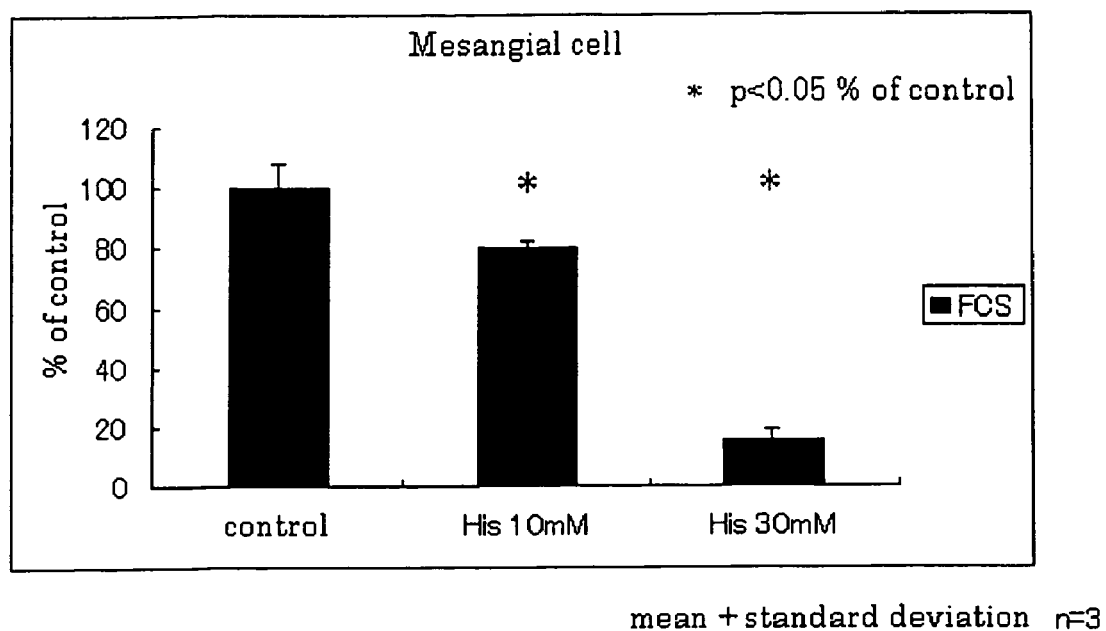

FIG. 6 depicts the results of the assay of BrdU uptake into cells reported in Example 6 (FCS addition), where mean+standard deviation (N=3);

*: $p<0.05$ by the t-test.

DETAILED DESCRIPTION OF THE PREFERRED EMBODIMENTS

Thus, in one aspect, the invention provides novel organ fibrosis inhibitors, such as a kidney fibrosis inhibitor, a pancreas fibrosis inhibitor, a lung fibrosis inhibitor, a vascular vessel fibrosis inhibitor, a skin fibrosis inhibitor, a bone marrow fibrosis inhibitor, and a liver fibrosis inhibitor, in which the organ fibrosis inhibitor contains histidine as an active ingredient, preferably histidine together with cysteine and/or cystine as active ingredients.

The cysteine, cystine, and histidine may individually be used in any of their L-forms, D-forms, and DL-forms. Additionally, the cysteine, cystine and histidine may be used, not only in their free forms, but also in their salt forms. The salt forms include acid addition salts and salts with bases. Preferably, salts of cysteine, cystine, and histidine acceptable as medical products or food or drink products are selected. Acids individually added to cysteine, cystine, and histidine to form salts acceptable as medical products or food or drink products include, for example, inorganic acids such as hydrogen chloride, hydrogen bromide, sulfuric acid, and phosphoric acid, and organic acids such as acetic acid, lactic acid, citric acid, tartaric acid, maleic acid, fumaric acid, and monomethylsulfuric acid. Examples of salts with bases which are acceptable as medical products or food or drink products of cysteine, cystine, and histidine include hydroxides or carbonates of metals such as sodium, potassium, and calcium, salts with inorganic bases such as ammonia, and salts with organic bases such as ethylenediamine, propylenediamine, ethanolamine, monoalkylethanolamine, dialkylethanolamine, diethanolamine, and triethanolamine.

As for the use of the organ fibrosis inhibitor, the organ fibrosis inhibitor can be used as a pharmaceutical agent for various organ diseases due to fibrosis. For example, the organ fibrosis inhibitor can be used in the form of a medical products such as a pharmaceutical agent for liver diseases (a pharmaceutical agent for use in the prophylaxis, amelioration and/or therapeutic treatment of liver diseases), particularly in the form of medical products for chronic hepatitis, cirrhosis, and liver cancer, or in the form used in food and/or drink products such as food products for health use and food products for sick individuals.

A pharmaceutical agent (including forms using food and/or drink products) containing at least histidine and exerting the action suppressing fibrosis for individual organs, for example an action suppressing liver fibrosis is encompassed within the scope of the present invention and can be blended and used with for example cysteine and/or cystine described above or other various types of necessary ingredients, unless these ingredients negatively affect the object of the present invention and the advantage (effect) obtained in accordance with the present invention (for example the auxiliary agents, carriers, and the like described below).

It has been reported that the liver damage due to D-galactosamine administration can be reduced in a rat given L-histidine (see, Sanada et al., *Biosci. Biotechnol. Biochem.*, vol. 63, pp. 319–322 (1999). However, it is nowhere indicated or suggested that histidine exhibited the effect of suppressing organ fibrosis, such as liver fibrosis.

Further, the effect of histidine on the suppression of the activation of Hepatic stellate cells due to the direct action on Hepatic stellate cells, or for example its action suppressing a liver fibrosis was never examined.

When cysteine and/or cystine is used in combination with histidine, the individual ingredients are preferably blended to a content ratio (molar ratio) of cysteine and/or cystine to histidine which is cysteine and/or cystine:histidine=1:0.1 to 10, preferably 1:0.2 to 8, more preferably 1:0.3 to 6 converted to their free forms. In this case, more satisfactorily, cystine is once calculated on a molar cysteine ratio basis.

When cysteine and/or cystine is used in combination with histidine, the cysteine and/or cystine and histidine as the organ fibrosis inhibitor may be used/administered individually separately and used in different forms. For example, the cysteine and/or cystine and histidine may be individually contained in two types of formulations and then used/administered as a set. Thus, all the amino acids to be used as the active ingredients may be contained in a single formulation form or a single food or drink product form for use. Alternatively, the amino acids to be used as the active ingredients may be separately used in two or more forms, for example two or three formulations and/or food and/or drink products. For example, the amino acids can be used in the following form: one of the amino acids can be used in a medical product, while the remaining amino acids can be used in a food and/or drink product.

In another aspect, the invention provides a combination of histidine with cysteine and/or cystine for use as an organ fibrosis inhibitor.

The plural active ingredients to be combined together typically may be used in one form which is a mixture, for example a combined agent. Additionally, the cysteine or cystine and histidine may be used separately in individual forms, for example different medical formulations or food and/or drink products; or the individual three types of cysteine, cystine and histidine, or a mixture of two thereof in one form and the remaining ingredient used individually in a separate form, for example different medical formulations or food and/or drink products.

Herein, the cysteine, cystine and histidine may suitably be individually in the L-form, D-form, or DL-form, or may be in salt forms.

Thus, possible embodiments include: (1) a combination of one of the active ingredients in a parenteral formulation and the remaining other active ingredients in an oral formulation; (2) a combination of one of the active ingredients in a medical formulation and the remaining other active ingredients in a food or drink product form; and (3) a combination of a first active ingredient in a parenteral formulation, a second active ingredient in an oral formulation, and a third active ingredient in a food or drink product.

Because the present invention encompasses the organ fibrosis inhibitor in accordance with the invention, all the descriptions about the invention in this specification are applicable to the description of this invention. Thus, the present invention encompasses each of the active ingredient units in separate medical products or food or drink products, and the present invention encompasses ingestion or administration of one or two of the active ingredients used in accordance with the present invention individually in separate ingestion or administration forms at individually separate timing and locations. The present invention can also be carried out in the same manner as the previously mentioned invention, referring to the descriptions of the invention in its specification.

Prior to now there has been no report or suggestion about the use of such a combination of histidine with cysteine and/or cystine to suppress organ fibrosis.

In another aspect, the invention provides a method for suppressing organ fibrosis by administering histidine, preferably histidine together with cysteine and/or cystine to a biological organism. Thus, the present invention also provides methods for therapeutically treating, ameliorating, and preventing diseases due to organ fibrosis and preventing the progress thereof, and the like, by administering histidine, preferably histidine together with cysteine and/or cystine to a biological organism.

When plural amino acids are administered to the biological organism as the active ingredients, there is no particular limitation on the relative timing of the administration of the individual plural amino acids. For example, all of the amino acids may be administered simultaneously or only one thereof may be administered separately. When all the three types of amino acids are used, the three types may be separately administered at intervals into the biological organism.

Herein, histidine may be in the L-form, D-form or DL-form, or may be in a salt form. Cysteine and cystine may each be in the L-form, D-form or DL-form or may each be in salt forms.

The dosage form to be used in the present method for inhibiting organ fibrosis can be selected from the organ fibrosis inhibitors of the present invention described above.

In an additional aspect, the present invention provides the use of histidine, preferably histidine and cystine and/or cystine for producing an organ fibrosis inhibitor. Once again, the cysteine, cystine, and histidine may individually be in the L-form, D-form or DL-form, or may individually be in salt forms.

In the case of a combination of active ingredients, typically, the plural active ingredients may be used in a state mixing all ingredients in one form, for example a combined agent. Additionally, histidine and cysteine and/or cystine to be used in combination are each separated and may be used in different forms, for example plural medical formulations and/or food or drink products. The forms of the amino acids to be used as the active ingredients in producing an organ fibrosis inhibitor can be selected from those described in connection with the organ fibrosis inhibitors in accordance with the present invention.

The various modes for carrying out the invention are now described below.

Organ fibrosis inhibitor:

In the pharmaceutical agent of the invention, histidine, preferably histidine together with cysteine and/or cystine, is used as the active ingredient to achieve the effect of suppressing the fibrosis of various organs, preferably the suppression of liver fibrosis. The pharmaceutical agent can exist in the form of a medical products or in the form of a food or drink product.

Concerning the liver, the applicable subjects are animals, particularly humans (patients with liver diseases and the like), in which liver diseases such as virus and alcoholic chronic hepatitis, other hepatitis (non-alcoholic steatohepatitis (NASH) and the like), liver fibrosis, cirrhosis, and liver cancer are to be prevented, ameliorated and/or therapeutically treated. Additionally, the applicable subjects include normal subjects, cattle and the like, for which the enhancement and control of liver function through food or drink products or feeds-by utilizing the action thereof is desired.

Concerning the kidney, the fibrosis suppressing action is utilized for animals, particularly humans (patients with kidney diseases, and the like), in which kidney diseases involving kidney fibrosis, such as diabetic nephropathy, glomerulonephritis, and nephrosclerosis are to be prevented, ameliorated and/or therapeutically treated. Additionally, the applicable subjects include normal subjects, cattle and the like, for which the enhancement and control of kidney function through food or drink products or feeds by utilizing the action thereof is desired.

Concerning the pancreas, the fibrosis suppressing action is utilized for animals, particularly humans (patients with pancreatic diseases, and the like) in which pancreatic diseases such pancreas fibrosis are to be prevented, ameliorated and/or therapeutically treated. Additionally, the applicable subjects include normal subjects, cattle and the like, for which the enhancement and control of pancreas function through food or drink products or feeds by utilizing the action thereof is desired.

Concerning the lung, the fibrosis suppressing action is utilized for animals, particularly humans (patients with lung diseases, and the like), in which lung diseases such lung fibrosis are to be prevented, ameliorated and/or therapeutically treated. Additionally, the applicable subjects include normal subjects, cattle and the like, for which the enhancement and control of lung function through food or drink products or feeds by utilizing the action thereof is desired.

Concerning vascular vessels, the action suppressing fibrosis is utilized for animals, particularly humans (patients with vascular degenerative diseases, and the like), in which fibrous vascular degenerative diseases such as arteriosclerosis or restenosis after vascular disobliteration following PTCA, shunt insertion, or the like are to be prevented, ameliorated and/or therapeutically treated. Additionally, the applicable subjects include normal subjects, cattle and the like, for which the enhancement and control of vascular function through food or drink products or feeds by utilizing the action thereof is desired.

Concerning skin, bone marrow, and other organs, the fibrosis suppressing action is utilized for animals, particularly humans (patients with fibrous organ degenerative diseases, and the like), in which diseases such pachyderma, keloid, bone marrow fibrosis and systemic sclerosis are to be prevented, ameliorated and/or therapeutically treated. Additionally, the applicable subjects include normal subjects, cattle and the like, for which the enhancement and control of the functions of the corresponding organs through food or drink products or feeds by utilizing the action thereof is desired.

The histidine, cysteine, and cystine, if they are to be used, can be prepared without any specific difficulty. Any of them can be prepared readily on the basis of the related art. Because the L-forms, D-forms and DL-forms thereof are commercially available products, these can be purchased and used conveniently.

When the cysteine, cystine and histidine are used in salt forms, the salts thereof (salts acceptable as medical products or food or drink products) can readily be prepared from their free forms, by utilizing known salt forming processes. As described above, the various salts that may be used include, for example, hydrochloride salts, sulfate salts, phosphate salts, citrate salts, sodium salts, and diethanolamine salts.

When the active ingredients to be used in accordance with the present invention are used as various pharmaceutical agents, for example, pharmaceutical agents for liver diseases, any formulation is satisfactory with no specific limitation. Thus, the pharmaceutical formulation may be an oral agent or a parenteral agent (injection). When the active ingredients are used in a food or drink product, generally, the ingredients are given orally. However, a specific non-oral ingestion approach (infusion) is also possible. A single formulation containing all the active ingredients to be used in accordance with the invention or formulations individually containing the active ingredients separately as described above may be used.

As to the amounts of the active ingredients for example for use in a pharmaceutical agent for liver diseases (a medical formulation), the amounts can be appropriately selected, depending on the symptoms and severity of a patient, the type of a dosage form and the like. When histidine is to be given, generally, the histidine can be used in case of oral administration at preferably about (approximately) 10 mg to 50 g, more preferably about (approximately) 100 mg to 20 g, still more preferably about (approximately) 1 to 10 g, based on its free form. When histidine is to be used for injection in a vein or the like, an amount about ¹⁄₂₀- to ½-fold the amount of the active ingredient for use in the oral formulation is satisfactory.

When the histidine is orally administered in combination with cysteine and/or cystine in the case of a mixture composition, the ratio of cysteine:histidine is suitably 1:0.1 to 1:10 (molar ratio, converted to free form). Alternatively, the mixture composition can be administered generally at preferably about 10 mg to 50 g, more preferably about 100 mg to 20 g, still more preferably about 1 to 10 g, based on the weight of the free forms of the amino acids contained therein. When the mixture composition is to be administered via injection into a vein and the like, the amount is suitably ¹⁄₂₀- to ½-fold the amount of the active ingredient used in the oral formulation.

When cystine is used in place of cysteine or is used together with cysteine, additionally, the corresponding amount can be selected readily with reference to the amount of cysteine used above. Because the administration of a combination of histidine with cysteine and the like is highly effective as compared to the administration of histidine alone, the same effect as in the former case can be obtained at a lower dose.

The amounts of the active ingredients to be used can reasonably be additionally increased in case of severe cases. As to the number and timing for the administration, the active ingredients may be administered once every few days or once daily but generally, the active ingredients are administered several times daily, for example in two to four divided doses, preferably after meals.

When the active ingredients are to be used in food or drink products, the amounts thereof to be blended in food or drink products can be determined on the basis of the oral dose described above.

As to the preparation of the formulation, the formulation may contain various other substances acceptable for the formulation of pharmaceuticals (as auxiliary agents and the like). The substances for the formulation can appropriately be selected, depending on the dosage of the formulation, and include for example excipients, diluents, additives, disintegrators, binders, coating agents, lubricants, sliding agents, smooth finishing agents, flavors, sweetening agents, and solubilizers. Specific examples of the substances for formulation include: magnesium carbonate, titanium dioxide, lactose, mannitol and other sugars, talc, milk protein, gelatin, starch, cellulose and derivatives thereof, animal and vegetable oils, polyethylene glycol, and solvents for example sterile water and monovalent or polyvalent alcohols such as glycerol.

As described above, the pharmaceutical agent of the invention may be prepared into various medical formulations which are presently known or may be developed in the future, for example various dosing forms for oral administration, parenteral (enteral) administration, transdermal administration, and inhalation. Any methods which are presently known or may be developed in the future can appropriately be used to prepare the pharmaceutical agent of the invention into these various medical formulations.

These various forms for medical formulations include for example appropriate solid or liquid formulation forms, for example granules, powders, coated tablets, tablets, (micro) capsules, suppositories, syrup, juice, suspensions, emulsions, drops, injection solutions, and formulations for sustained release of active substances.

Of course, the pharmaceutical agent of the present invention in the formulation forms listed above should contain the ingredients (L-histidine, and L-cysteine/L-cystine and L-histidine in case of combination, and the like) in amounts effective for exerting their pharmaceutical action.

Even in case of using ingredients in addition to those described above, a formulation can be prepared which meets the requirements of each dosage form, on the based on the above specifications or by utilizing known formulation techniques.

The descriptions about the pharmaceutical agent for oral use and others can be referred to in order to apply the present invention to food and/or drink products.

When the active ingredients to be used in the organ fibrosis inhibitor of the invention are to be prepared into separate products (medical formulations, food or drink products, and the like) or when a mixture of two of the active ingredients and the remaining active ingredient are to be prepared into separate products (the combination of the invention), the preparation can be prepared easily on the basis of the descriptions above.

Thus, separate aspects of the invention include the following:

(A) a combination of histidine with cysteine and/or cystine characterized in that it is used in an organ fibrosis inhibitor, or a combination of histidine with cysteine and/or cystine as an organ fibrosis inhibitor;

(B) a method for suppressing organ fibrosis characterized in that histidine, preferably histidine with cysteine and/or cystine, is administered to a biological organism (including a treatment method for the therapeutic treatment, amelioration, progress prevention, and prophylaxis (prevention) of diseases due to an organ fibrosis and the like);

(C) use of histidine, preferably cysteine and/or cystine and histidine for producing an organ fibrosis inhibitor; and the like.

These inventions all can be readily practiced as well with reference to the descriptions about the organ fibrosis inhibitor of the invention and on the basis of the following Examples and the like, and with reference to techniques that are known, if necessary.

Other features of the invention will become apparent in the course of the following descriptions of exemplary embodiments which are given for illustration of the invention and are not intended to be limiting thereof.

EXAMPLES

Example 1

Figure 1:
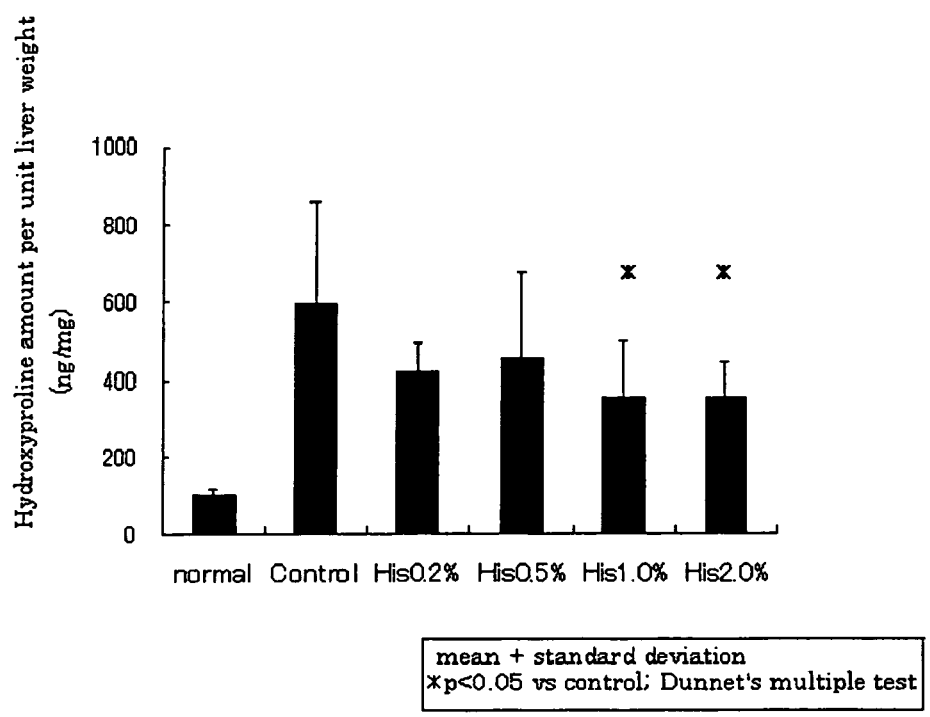
FIG. 1 depicts the results of the assay of liver hydroxyproline (Hyp) reported in Example 1, where normal: non-treated group.

Dimethylnitroseamine (DMN) was administered intraperitoneally at 10 mg/kg three times weekly to a male 9-week-old SD rat for 3 weeks to induce liver fibrosis. A commercially available feed or experimental diets prepared by adding L-histidine (His) as a test substance at concentrations of 0.2, 0.5, 1.0, and 2.0 wt. % to a commercially available feed were fed beginning on the day of start of DMN administration and thereafter. On day 21 from the start of the DMN administration, the liver was collected to assay the amount of hydroxyproline (Hyp) in the liver as a liver fibrosis marker, using an amino acid analyzer. The results are shown in FIG. 1. As is clearly shown in FIG. 1, the amount of Hyp in the liver, which increased by about 6 fold via the DMN administration, was significantly decreased via oral His administration.

Example 2

Hepatic stellate cells were isolated from a male Wistar rat liver and were cultured by the liver perfusion method with pronase E and collagenase. Hepatic stellate cells on day 8 to day 14 were cultured overnight in a culture medium containing 10 vol. % fetal calf serum (FCS). The culture medium was replaced with a culture medium containing 0.1 vol. % FCS, and it was cultured for 48 hours. Subsequently, L-histidine as the test substance was added in an amount to give a concentration of 1 to 30 mM. Then, further, platelet-derived growth factor (PDGF) was added to give a final concentration of 25 ng/ml, and the Hepatic stellate cells were cultured for 24 hours. Six hours before the completion of the culturing, bromodeoxyuridine (BrdU) was added to the culture system. After the completion of the culturing, the BrdU uptake into the cells was assayed by ELISA (enzyme-linked immunosorbent assay). As a control, only PDGF (at the final concentration of 25 ng/ml) was added to the culture medium. When the BrdU uptake in the control was defined as 100%, the value of each of the groups was calculated and the results are shown in FIG. 2. These results show that L-histidine strongly suppressed the DNA synthesis of Hepatic stellate cells activated with PDGF in a dose-dependent manner.

Example 3

In the same manner as in Example 2, the effects of L-histidine and D-histidine (individually at 30 mM) on the DNA synthesis of Hepatic stellate cells were compared with each other. When the BrdU uptake in the control was defined as 100%, the value of each of the groups was calculated and is shown in FIG. 3. The results show that L-histidine and D-histidine both strongly suppressed the DNA synthesis of Hepatic stellate cells activated with PDGF, and the levels of the suppression were almost equal.

Example 4

Hepatic stellate cells were isolated from male Wistar rat liver, and were cultured by the liver perfusion method with pronase E and collagenase. Hepatic stellate cells on day 8 to day 14 were cultured overnight in a culture medium containing 10 vol. % fetal calf serum (FCS). The culture medium was replaced with a 0.1 vol. % FCS culture medium, and it was cultured for 48 hours. Subsequently, L-cysteine, L-histidine or a composition of L-cysteine and L-histidine as a test substance was added thereto. Then, further, platelet-derived growth factor (PDGF) was added to give a final concentration of 25 ng/ml, for culturing the Hepatic stellate cells for 24 hours. Six hours before the completion of the culturing, bromodeoxyuridine (BrdU) was added to the culture system. After the completion of the culturing, the BrdU uptake into the cells was assayed by ELISA (enzyme-linked immunosorbent assay). As a control, only PDGF (at the final concentration of 25 ng/ml) was added to the culture medium. When the BrdU uptake in the control was defined as 100%, the value of each of the groups was calculated and the results are shown in FIG. 4. It is clear from the results that the mixture (composition) of L-cysteine and L-histidine strongly suppresses the DNA synthesis of Hepatic stellate cells with PDGF, compared with L-cysteine or L-histidine alone.

Example 5

Human normal lung fibroblast cells (HLF-1 cell) were cultured overnight in a culture medium containing 10 vol. % fetal calf serum (FCS). Subsequently, the culture medium was replaced with a 0.1 vol. % FCS culture medium, and it was cultured for 24 hours. Subsequently, L-histidine (His) as the test substance was added so that the concentration was 10 or 30 mM. Then, further, platelet-derived growth factor (PDGF) was added to give a final concentration of 25 ng/ml or FCS was added to give a final concentration of 5 vol. %, and the HLF-1 cells were cultured for 24 hours. Six hours before the completion of the culturing, bromodeoxyuridine (BrdU) was added to the culture system. After the completion of the culturing, the BrdU uptake into the cells was assayed by ELISA (enzyme-linked immunosorbent assay). As a control, only PDGF (at the final concentration of 25 ng/ml) or FCS (at the final concentration of 5 vol. %) was added to the culture medium. When the BrdU uptake in the control was defined as 100%, the value of each of the groups is shown in FIG. 5. The results revealed that L-histidine strongly suppressed the DNA synthesis of the human normal lung fibroblast cell with PDGF or FCS.

Example 6

Human kidney mesangial cells were cultured overnight in a culture medium containing 10 vol. % fetal calf serum (FCS). Subsequently, the culture medium was replaced with a 0.1 vol. % FCS culture medium, and it was cultured for 24 hours. Subsequently, L-histidine (His) as a test substance was added in an amount to give a concentration of 10 or 30 mM. Then, further, FCS was added to give a final concentration of 5 vol. %, and the mesangial cells were cultured for 24 hours. Six hours before the completion of the culturing, bromodeoxyuridine (BrdU) was added to the culture system. After the completion of the culturing, the BrdU uptake into the cells was assayed by ELISA (enzyme-linked immunosorbent assay). As a control, only 5 vol. % FCS was added to the culture medium. When the BrdU uptake in the control was defined as 100%, the value of each of the groups was calculated and the results are shown in FIG. 6. The result show that L-histidine strongly suppressed the DNA synthesis of the human kidney mesangial cell with FCS.

ADVANTAGES OF THE INVENTION

In accordance with the present invention, an excellent organ fibrosis inhibitor, particularly a liver fibrosis inhibitor, containing histidine as the active ingredient, preferably histidine together with cysteine and/or cystine as the active ingredients, is provided. Other than the use in forms of pharmaceutical agents (medical products) for liver diseases, for example chronic hepatitis, liver fibrosis, cirrhosis and liver cancer, the organ fibrosis inhibitor, particularly the liver fibrosis inhibitor, can be used in various foods, particularly in food and/or drink products for health use and food products for sick individuals, in the case when the amino acids which are the active ingredients are used in their L-forms.

Histidine, particularly preferably in combination with cysteine and/or cystine, exerts a significant suppression organ fibrosis, particularly liver fibrosis, and therefore, histidine, alone, or combined with cysteine and/or cystine for concurrent or separate use, can be used in the form of a medical product or in the form of food or drink products.

When the active ingredients are used in combination, cysteine and/or cystine and histidine may used in forms separate from each other, for example in separate formulations or in separate food or drink products; or the individual three types of cysteine, cystine and histidine; or a mixture of two types thereof and the remaining one type may be used in separate forms, for example in different formulations or food or drink products.

Further, the present invention also provides: (1) methods for suppressing organ fibrosis (including a method for the therapeutic treatment, amelioration, progress prevention, and prophylaxis of diseases due to an organ fibrosis in biological organisms, and the like); (2) methods of producing an organ fibrosis inhibitor (including forms of medical products, food and/or drink products and the like) from the active ingredients; and (3) an organ fibrosis inhibitor containing a combination of the plural active ingredients.

Thus, the present invention can be widely used in the fields of medical products, food products and the like, and therefore, the invention is very useful industrially.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for suppressing organ fibrosis, comprising administering to a subject in need thereof an effective amount of a composition comprising one or more amino acids and one or more additives,
   wherein said composition comprises histidine and said histidine is at least one member selected from the group consisting of L-histidine, D-histidine, DL-histidine, salts thereof, and mixtures thereof, and
   wherein the only amino acids present in the composition are selected from the group consisting of histidine, cysteine, and cystine.

2. The method of claim 1, wherein said organ fibrosis is kidney fibrosis, pancreas fibrosis, lung fibrosis, vascular vessel fibrosis, skin fibrosis, bone marrow fibrosis, or liver fibrosis.

3. The method of claim 1, wherein said organ fibrosis is liver fibrosis.

4. The method of claim 1, wherein said subject in need thereof suffers from at least one liver disease selected from the group consisting of chronic hepatitis, liver fibrosis, cirrhosis, liver cancer, and non-alcoholiic steatohepatitis.

5. The method of claim 1, wherein said histidine is administered in the form of a food or drink product.

6. The method of claim 1, wherein said histidine is administered orally or parenterally.

7. The method of claim 1, further comprising administering at least one further active agent selected from the group consisting of L-cysteine, D-cysteine, DL-cysteine, L-cystine, D-cystine, DL-cystine, salts thereof, and mixtures thereof to said subject in need thereof.

8. The method of claim 7, where said at least one further active agent and said histidine are administered in separate dosage forms.

9. The method of claim 7, wherein said at least one further active agent and said histidine are administered in a single dosage form.

10. The method of claim 7, which comprises administering said histidine and said at least one further active agent in a molar ratio of cysteine:histidine of 1:0.1 to 10.

11. The method of claim 1, wherein said subject in need thereof is a human.

12. The method of claim 11, further comprising administering at least one further active agent selected from the group consisting of L-cysteine, D-cysteine, DL-cysteine, L-cystine, D-cystine, DL-cystine, salts thereof, and mixtures thereof to said subject in need thereof.

13. The method of claim 12, where said at least one further active agent and said histidine are administered in separate dosage forms.

14. The method of claim 12, wherein said at least one further active agent and said histidine are administered in a single dosage form.

15. The method of claim 11, comprising administering said histidine to said human in an amount of 10 mg to 50 g per day.

16. The method of claim 15, wherein said human is suffering from at least one liver disease selected from the group consisting of chronic hepatitis, liver fibrosis, cirrhosis, liver cancer, and non-alcoholic steatohepatitis.

17. The method of claim 11, comprising administering said histidine to said human in an amount of 100 mg to 20 g per day.

18. The method of claim 17, wherein said human is suffering from at least one liver disease selected from the group consisting of chronic hepatitis, liver fibrosis, cirrhosis, liver cancer, and non-alcoholic steatohepatitis.

19. The method of claim 18, comprising administering said histidine to said human in an amount of 1 to 10 g per day.

20. The method of claim 19, wherein said human is suffering from at least one liver disease selected from the group consisting of chronic hepatitis, liver fibrosis, cirrhosis, liver cancer, and non-alcoholic steatohepatitis.

21. The method of claim 1, wherein histidine is the only amino acid in said composition and, wherein said histidine is at least one member selected from the group consisting of L-histidine, D-histidine, DL-histidine, salts thereof, and mixtures thereof.

* * * * *